United States Patent [19]

Sekine et al.

[11] 4,434,159

[45] Feb. 28, 1984

[54] PHARMACEUTICAL COMPOSITION FOR INTRARECTAL ADMINISTRATION, AND SUPPOSITORY PREPARED THEREFROM

[75] Inventors: Kunio Sekine; Yoshiki Suzuki, both of Hino; Gentaro Yamashita, Tachikawa; Hisao Yamaguchi, Hino, all of Japan

[73] Assignee: Teijin Limited, Osaka, Japan

[21] Appl. No.: 249,462

[22] Filed: Mar. 31, 1981

[30] Foreign Application Priority Data

Mar. 31, 1980 [JP] Japan .................................. 55-40368
Mar. 31, 1980 [JP] Japan .................................. 55-40369

[51] Int. Cl.³ .................. A61K 37/26; A61K 31/725;
A61K 31/70; A61K 37/00
[52] U.S. Cl. .................................. 424/178; 424/183;
424/180; 424/177; 424/DIG. 15
[58] Field of Search ............... 424/178, 183, DIG. 15, 424/180, 177

[56] References Cited

U.S. PATENT DOCUMENTS

| 4,156,719 | 5/1979 | Sezaki et al. | 424/183 |
| 4,164,573 | 8/1979 | Galinsky et al. | 424/178 |
| 4,277,465 | 7/1981 | Kamada | 424/178 |

FOREIGN PATENT DOCUMENTS

| 9609 | 4/1980 | European Pat. Off. | |
| 55-8485 | of 1980 | Japan. | |
| 55-8486 | of 1980 | Japan. | |
| 55-38925 | of 1980 | Japan. | |
| 1462399 | 1/1977 | United Kingdom | 424/246 |
| 1563311 | 3/1980 | United Kingdom | 424/178 |

*Primary Examiner*—Frederick E. Waddell
*Attorney, Agent, or Firm*—Wenderoth, Lind & Ponack

[57] ABSTRACT

A pharmaceutical composition for intrarectal administration comprising a pharmaceutically effective amount of an active ingredient which when administered alone to the rectum, is substantially unabsorbable into the living body through the mucous membrane of the rectum, said composition further containing an absorption aid acting within the rectum in such a way as to induce absorption of said active ingredient through the rectal mucous membrane, said absorption aid being characterized by (1) being substantially nontoxic to living organisms, (2) containing in the molecule at least two hydrophilic groups selected from the class consisting of carboxyl groups, acidic hydroxyl groups, carboxyl groups in the form of pharmaceutically acceptable salts, acidic hydroxyl groups in the form of pharmaceutically acceptable salts, carboxyl groups in the form of amides and acidic hydroxyl groups in the form of esters, (3) containing in the molecule at least two lipophilic groups selected from the class consisting of groups of the formulae

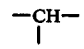

and -CH$_2$-, the number of the lipophilic groups being not less than that of the hydrophilic groups, and (4) having a molecular weight of from about 100 to about 300; and a suppository prepared therefrom in unit dosage form.

15 Claims, No Drawings

PHARMACEUTICAL COMPOSITION FOR INTRARECTAL ADMINISTRATION, AND SUPPOSITORY PREPARED THEREFROM

This invention relates to a pharmaceutical composition for intrarectal administration, and to a suppository prepared therefrom in unit dosage form.

Drugs have been administered widely by peroral methods using tablets, capsules, granules, syrups, etc., injecting methods using injecting preparations for subcutaneous, intramuscular, intravenous and other routes, and topical methods using nasal drops, eye drops, ointments, creams, etc.

One method which has attracted increasing attention recently comprises administering a drug to the rectum to allow it to be absorbed through the rectal mucous membrane. The reason for this is that the intrarectal administration generally has the following advantages.

(1) Frequently, side-effects of drugs can be avoided. In intrarectal administration, side-effects such as gastrointestinal disorders by oral administration or muscular constriction by intramuscular administration can be avoided almost completely.

(2) In many cases, the ratio of an administered drug utilized in vivo is frequently high. Since acids or enzymes scarcely exist in the rectum in normal condition, the drug remains substantially undecomposed in the rectum before absorption. Furthermore, because more than half of the drug absorbed from the rectum first moves with blood streams which do not pass through the liver, the absorbed drug can be prevented from being metabolized and inactivated in the liver in contrast to the case of oral administration in which the absorbed drug moves with blood streams which flow through the liver. In oral administration the ratio of utilization of the administered drug frequently differs depending upon the time of administration, namely whether it is before or after each meal or between meals, but this never occurs in intrarectal administration. Furthermore, absorption of the administered drug is better than in oral administration.

(3) The administration is relatively simple and accurate, and there is no restriction as to the time of administration. The administration can be effected even during nausea, vomiting or unconsciousness, or after surgical operation.

The intrarectal administering method having such advantages, however, is still desired to be improved in various respects.

Generally, drugs having a relatively high molecular weight, for example peptides such as insulin and calcitonin or polysaccharides such as heparin are scarcely absorbed at least substantially through the rectal mucous membranes. Accordingly, patients with diabetes, for example, are compelled to have shots of insulin every day. In view of this situation, some attempts have been proposed to allow drugs of relatively high molecular weight to be absorbed through the rectal mucous membrane. For example, Japanese Patent Publication No. 8485/1980 discloses a preparation for intrarectal administration comprising a mixture of insulin with at least one material selected from phospholipids, bile acids and alkali metal salts of bile acids. Japanese Patent Publication No. 8486/1980 describes a preparation comprising a mixture of insulin with at least one surfactant selected from ether-type nonionic, anionic, cationic and amphoteric surface-active agents with or without at least one material selected from phospholipids, bile acids and alkali metal salts of bile acids.

Japanese Patent Publication No. 38925/1980 describes a preparation for intrarectal administration comprising a dispersion of Cephalexin in a mixture of an oily or water-soluble substrate and a surface-active agent.

None of these patent documents, however, make it clear why the presence of phospholipids or surfactants promotes absoprtion of insulin or Cephalexin from the mucous membranes of the rectum.

Japanese Laid-Open Patent Publication No. 31,040/1980 discloses a drug for absorption through the digestive tract, comprising a therapeutically effective ingredient and an enamine derivative of the formula

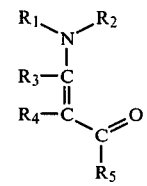

wherein

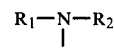

is a residue resulting from removal of one hydrogen atom from the amino group of an organic aminocarboxylic acid or an organic aminosulfonic acid, the carboxyl group or sulfo group in the residue may be in the form of an alkali metal salt or ester, and $R_1$ and $R_2$ may partly join together to form a cyclic group; $R_3$ represents a hydrogen atom, or a lower alkyl or lower alkoxy group; $R_4$ represents a hydrogen atom or a lower alkyl or lower alkoxycarbonyl group; and $R_5$ represents a lower alkyl or lower alkoxy group, provided that when both $R_3$ and $R_4$ are lower alkyl groups, they may be bonded to each other to form a carbocyclic group, and when $R_4$ is a lower alkyl group and $R_5$ is a lower alkoxy group, they may be bonded to each other to form an oxygen-containing alicyclic group.

The above general formula encompasses a number of compounds, but in view of the compounds specifically disclosed in the above patent document, especially from the working examples therein, it appears that enamine derivatives of the following formula

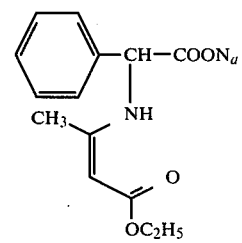

especially promote absorption of antibacterial agents such as Ampicillin, Cephalothin and Cephalexin, or insulin in the rectum. The patent document, however, fails to give any description about the safety of these enamine derivatives, and the inventors of the present application, too, do not know much about their safety.

It is an object of this invention to provide an absorption aid for inducing effective absorption through the rectal mucous membrane of an active ingredient which when administered alone to the rectum, is not substantially absorbed through the rectal mucous membrane.

Another object of this invention is to provide a pharmaceutical composition suitable for intrarectal administration comprising the aforesaid active ingredient and the absorption aid.

Still another object of this invention is to provide an absorption aid which induces effective absorption of the aforesaid active ingredient through the mucous membrane of the rectum and of which safety has been determined.

Yet another object of this invention is to provide a highly safe pharmaceutical composition suitable for intrarectal administration, comprising the aforesaid active ingredient and the aforesaid highly safe absorption aid.

A further object of this invention is to disclose absorption aids, which exhibit the above properties, from the standpoint of their chemical structures.

The objects and advantages of this invention are achieved by a pharmaceutical composition for intrarectal administration comprising a pharmaceutically effective amount of an active ingredient which when administered alone to the rectum, is substantially unabsorbable into the living body through the mucous membrane of the rectum, said composition further containing an absorption aid acting within the rectum in such a way as to induce absorption of said active ingredient through the rectal mucous membrane, said absorption aid being characterized by (1) being substantially nontoxic to living organisms, (2) containing in the molecule at least two hydrophilic groups selected from the class consisting of carboxyl groups, acidic hydroxyl groups, carboxyl groups in the form of pharmaceutically acceptable salts, acidic hydroxyl groups in the form of pharmaceutically acceptable salts, carboxyl groups in the form of amides and acidic hydroxyl groups in the form of esters, (3) containing in the molecule at least two lipophilic groups selected from the class consisting of groups of the formulae

and —CH$_2$—, the number of the lipophilic groups being not less than that of the hydrophilic groups, and (4) having a molecular weight of from about 100 to about 300.

The active ingredient used in the composition of the invention is not substantially absorbable into the living body through the mucous membrane of the rectum when administered alone to the rectum. The substantial unabsorbability of the active ingredient into the living body means that the active ingredient shows no pharmacological efficacy of the active ingredient despite the fact that if it is absorbed into the living body, its pharmacological efficacy according to the absorption should be exhibited.

Generally, the active ingredient used in this invention has a molecular weight of at least about 330, preferably at least about 1,000. Examples of the active ingredient that can be used in this invention include peptide hormones such as calcitonin, secretin, vasopressin, insulin, angiotensin, felypressin, thyrotropin release hormone, gonadotropin release hormone, corticotropin, prolactin, somatotropin, thyrotropin, luteinizing hormone (LH), callicrein, parathyrin, glucagon, oxytocin, gastrin and serum gonadotropin, and polysaccharides such as heparin sodium, heparin calcium and chondroitin sulfate.

Usually one kind of such active ingredient is included in the pharmaceutical composition of this invention. If desired, two or more kinds of active ingredients may be included together.

Calcitonin, insulin and heparin sodium or calcium are the preferred active ingredients for use in the invention.

The absorption aid used in this invention, when administered to the rectum together with the active ingredient, acts within the rectum in such a way as to induce absorption of the active ingredient into the living body through the rectal mucous membrane. Although the detailed mechanism of the absorption aid has not been elucidated, investigations of the present inventors have shown that such an absorption aid should contain specified hydrophilic groups and lipophilic groups in a certain correlation and have a molecular weight within a specified range.

Specifically, the absorption aid used in this invention is characterized by (1) being substantially nontoxic to living organisms, (2) containing in the molecule at least two hydrophilic groups selected from the class consisting of carboxyl groups, acidic hydroxyl groups, carboxyl groups in the form of pharmaceutically acceptable salts, acidic hydroxyl groups in the form of pharmaceutically acceptable salts, carboxyl groups in the form of amides and acidic hydroxyl groups in the form of esters, (3) containing in the molecule at least two lipophilic groups selected from the class consisting of groups of the formulae

and —CH$_2$—, the number of the lipophilic groups being not less than that of the hydrophilic groups, and (4) having a molecular weight of from about 100 to about 300.

The absorption aid contains at least two each of the specified hydrophilic groups and lipophilic groups in the molecule, provided that the number of the lipophilic groups is not less than that of the hydrophilic groups.

The absorption aid of this invention should have a molecular weight of about 100 to about 300, preferably about 100 to about 250.

Compounds which meet the above conditions in regard to hydrophilic and lipophilic groups but have molecular weights outside the specified range do not promote, substantially or to the expected degree, the absorption of active ingredients of relatively high molecular weights contemplated in the present invention.

In the present invention, absorption aids having two hydrophilic groups in the molecule are preferably used.

The hydrophilic groups are basically carboxyl groups or acidic hydroxyl groups. The carboxyl groups may be in the form of pharmaceutically acceptable salts, or amides, and the acidic hydroxyl groups may be in the form of pharmaceutically acceptable salts, or esters.

The acidic hydroxyl group denotes a hydroxyl group bonded to a carbon atom which is bonded to another adjacent carbon atom through a double bond. A typical example of such an acidic hydroxyl group is a phenolic hydroxyl group, or a hydroxyl group at the 4- or 5-position in the 4,5-dehydro product of a five-membered lactone.

The lipophilic groups denote

and —CH$_2$—. Two of the three bonds of the group

may be bonded respectively to two different adjacent atoms, or to one adjacent atom forming a double bond.

Preferred absorption aids for use in this invention may, for the sake of convenience, be classified into the following three groups by the types of the two hydrophilic groups.

(1) Absorption aids wherein the two hydrophilic groups are either acidic hydroxyl groups, acidic hydroxyl groups in the form of pharmaceutically acceptable salts, or acidic hydroxyl groups in the form of esters.

(2) Absorption aids wherein one of the two hydrophilic groups is either a carboxyl group, a carboxyl group in the form of a pharmaceutically acceptable salt, or a carboxyl group in the form of an amide, and the other is either an acidic hydroxyl group, an acidic hydroxyl group in the form of a pharmaceutically acceptable salt, or an acidic hydroxyl group in the form of an ester.

(3) Absorption aids wherein the two hydroxyl groups are either carboxyl groups, carboxyl groups in the form of pharmaceutically acceptable salts, or carboxyl groups in the form of amides.

It is believed that these absorption aids exhibit almost equivalent actions for the objects of this invention. If one is compelled to rank them, however, the absorption aids in groups (1) and (2) above would be the preferred species as they exhibit equally satisfactory actions irrespective of the types of the active ingredients.

The pharmaceutically acceptable salts are preferably the sodium or potassium salts. The acidic hydroxyl group in the form of an ester denotes an ester group formed between the acidic hydroxyl group with, for example, a lower aliphatic monocarboxylic acid such as acetic acid.

Examples of the absorption aids of group (1) are ascorbic acids, such as ascorbic acid, sodium ascorbate and potassium ascorbate.

Examples of the absorption aids of groups (2) include salicyclic acid, sodium salicylate, potassium salicylate, acetyl-salicylic acid, salicylosalicylic acid, aluminum acetylsalicylate, choline salicylate, salicylamide, lysine acetylsalicylate, exalamide, diflunisal and ethenzamide.

Preferably, the absorption aids of group (3) are compounds having an amino group, or acidic amino acids. Specific examples include glutamic acid, sodium glutamate, potassium glutamate, glutamine, pyroglutamic acid, sodium pyroglutamate, potassium pyroglutamate, pyroglutamic acid triethanolamine salt, aspartic acid, sodium aspartate, potassium aspartate, and asparagine.

The exemplified compounds of group (1) are known as food additives, and the exemplified compounds of groups (2) and (3) are either pharmaceuticals, food additives or components of living organisms. Accordingly, the safety of these compounds has been ascertained.

The pharmaceutical composition for intrarectal administration in accordance with this invention contains the aforesaid active ingredient and adsorption aid, and is usually in the form of a liquid or solid with these components dissolved or dispersed in a base.

The pharmaceutical composition of this invention should contain the active ingredient in a pharmaceutically effective amount. Suitable pharmaceutically effective amounts differ depending upon the active ingredients, the condition of a subject to which the composition is to be administered, the duration of administration, etc. The content of the active ingredient per unit dosage will be determined depending upon the number of unit dosages for a certain fixed period, for example one day, by considering the desired dosage of the active ingredient.

Calcitonin may be administered in a dosage of about 0.7 to about 100 MRC units/kg body weight.day, preferably about 0.7 to about 35 MRC units/kg of body weight.day. Accordingly, one suppository for administration to a human having a body weight of 60 kg two times a day may contain calcitonin in an amount of about 20 to about 3,000 MRC units, preferably about 20 to about 1,000 MRC units.

For example, insulin may be administered in a dosage of about 0.1 to about 17.5 units/kg of body weight.day, preferably about 0.25 to about 12.5 units/kg of body weight.day. Accordingly, one suppository for administration to a human having a body weight of 60 kg three times a day may contain about 2 to about 350 units, preferably about 5 to about 250 units, of insulin.

Likewise, heparin can be administered in an amount of about 17 to about 3,300 units/kg of body weight.day, preferably about 17 to about 1,670 units/kg of body weight.day. Hence, one suppository for administration to a human having a body weight of 60 kg two times a day may contain about 500 to about 100,000 units, preferably about 500 to about 50,000 units, of heparin.

The absorption aid may be included in the composition of this invention in an amount effective for promotion of absorption of the active ingredient. The amount may be determined by animal experiments using a specified combination of the active ingredient and the absorption aid. Experiments of the present inventors have shown that if the absorption aid is a pharmaceutical of which usual dose is known, its effective amount may be not more than one-fifth of the usual dose.

Thus, the pharmaceutical composition of this invention may contain the absorption aid in an amount of about 0.1 to about 40% by weight, preferably about 0.2 to about 20% by weight, based on the composition.

The base used in the pharmaceutical composition of this invention may be those which are known as bases of suppositories for intrarectal administration. Examples of the base include oils and fats comprising triglycerides as main components such as cacao butter, palm fat, palm kernel oil, coconut oil, fractionated coconut oil, lard and WITEPSOL ®, waxes such as lanolin and reduced lanolin; hydrocarbons such as Vaseline, squalene, squalane and liquid paraffin; long to medium chain fatty acids such as caprylic acid, lauric acid, stearic acid and oleic acid; higher alcohols such as lauryl alcohol, cetanol and stearyl alcohol; fatty acid esters such as butyl stearate and dilauryl malonate; medium to long chain carboxylic acid esters of glycerin such as triolein and tristearin; glycerin-substituted carboxylic acid esters such as glycerin acetoacetate; and polyethylene glycols and its derivatives such as macrogols and cetomacrogol. They may be used either singly or in combination of two or more.

The WITEPSOL, cacao butter, glycerides, and polyethylene glycols are preferred.

If desired, the composition of this invention may further include a surface-active agent, a preservative, a coloring agent, a flavoring agent, etc., which are ordinarily used in suppositories.

Preferred unit dosage forms of the pharmaceutical composition of this invention include a solid suppository having as a base a solid fat which when administered to the rectum, becomes flowable within the rectum, such as cacao butter and WITEPSOL, a solid suppository having as a base a hydrophilic solid substance which becomes flowable in the rectum in the same way, such as macrogol, and a gelatin capsule suppository having a nomally liquid substance (liquid at room temperature) such as neutral fatty acid triglycerides and vegetable oils as a base and coated with a gelatin film.

The pharmaceutical complosition of this invention may be prepared by uniformly mixing predetermined amounts of the active ingredient, the absorption aid and optionally the base, etc. in a stirrer or a grinding mill, if required at an elevated temperature. The resulting composition, may be formed into a suppository in unit fosage form by, for example, casting the mixture in a mold, or by forming it into a gelatin cupsule using a capsule filling machine.

The following Examples illustrate the present invention more specifically. It should be understood that the examples are merely for illustrative purposes and do not intend to limit the scope of the invention.

EXAMPLE 1

This example is for the purpose of showing that the composition of this invention induces efficient absorption of an active ingredient which in normal intrarectal administration is scarcely absorbable from the mucous membrane of the rectum, and that the composition of the invention is safe.

The example includes (a) a test on absorption of calcitonin as an active ingredient of a suppository, (b) a test on the effect of the amount of the absorption aid used in this invention on the absorption of the active ingredient, and (c) a test on the safety of the absorption aid. (a) About 14 g of each of the absorption aids shown in Table 1 was added to 186 g of cacao butter, and they were well mixed by a grinder. Salmon caltintonin or [Asu$^{1,7}$]-eel calcitonin was added gradually and mixed to form a homogeneous composition. The composition was slightly heated to make it flowable, and about 80 mg of it was cast into a suppository container made for rats, and allowed to solidify by cooling to obtain a rat suppository having a diameter of about 3 mm and a length of about 6 mm. The suppository contained 0.7 MRC units of calcitonin.

The suppository was administered to the rectum of each of SV male rats (body weight about 200 g) and the concentration of calcium in the serum was measured 1, 2, 3, and 5 hours later to examine the absorbabillity of calcitonin from the rectum. The calcium level in the serum was measured by using a calcium level measuring kit of Yatoron Co., and five rats were used for each blood withdrawal. The results are shown in Table 1 as the decrease (%) of the serum calcium level from that before administration of the calcitonin-containing suppository.

As controls, a suppository not containing the absorption aid, and a suppository containing an enamine derivative of phenylglycine or a surface-active agent in almost the same amount as the absorption aid were produced, and subjected to the same test as above.

Furthermore, [Aus$^{1,7}$]-eel calcitonin was intramuscularly injected to rats, and the decrease in serum calcium level was also examined.

The results are shown in Table 1.

The results demonstrate that when the suppositories containing the absorption aids in accordance with this invention are administered, a marked decrease in serum calcium level is noted as compared with the control suppository not containing any absorption aid, and the same or further decrease in serum calcium level is noted as compared with the administration of the suppositories containing the enamine derivative of amino acid and the surface-active agent instead of the absorption aids. It is also noted that when compared with the intramuscular injection, the intrarectal administration of about 4 to 5 times as large an amount of calcitonin is expected to produce an equivalent effect to injection.

The MRC unit of calcitonin corresponds to 1,000 times the amount of calcitonin required to decrease the serum calcium level by about 1% in a male rat having a body weight of 150 g after the lapse of one hour from intravenous injection of calcitonin into the rat which had been caused to fast for 24 hours.

TABLE 1

| | Suppository | Decrease of the serum calcium level | Decrease (%) in serum calcium level from that before administration (measured after the lapse of) | | | |
|---|---|---|---|---|---|---|
| | | | 1 hour | 2 hours | 3 hours | 5 hours |
| Invention | Salmon calcitonin | 0.7 u/sup | 33.1 | 29.3 | 22.1 | 2.5 |
| | Ascorbic acid | 7.0% | | | | |
| | Cacao butter | 93.0% | | | | |
| | [Asu$^{1.7}$]eel calcitonin | 0.7 u/sup | 30.9 | 26.9 | 21.7 | 2.2 |
| | Sodium ascorbate | 7.1% | | | | |
| | Cacao butter | 92.9% | | | | |
| | Salmon calcitonin | 0.7 u/sup | 29.6 | 28.4 | 21.3 | 4.1 |
| | Sodium salicylate | 7.0% | | | | |
| | Cacao butter | 93.0% | | | | |
| | [Asu$^{1.7}$]eel calcitonin | 0.7 u/sup | 30.2 | 27.5 | 19.7 | 2.4 |
| | Acetylsalicylic acid | 7.0% | | | | |
| | Cacao butter | 93.0% | | | | |
| | [Asu$^{1.7}$]eel calcitonin | 0.7 u/sup | 30.1 | 26.5 | 18.7 | 2.2 |
| | Glutamic acid | 7.1% | | | | |

TABLE 1-continued

Decrease of the serum calcium level

| | Suppository | | \multicolumn{4}{c}{Decrease (%) in serum calcium level from that before administration (measured after the lapse of)} |
|---|---|---|---|---|---|---|
| | | | 1 hour | 2 hours | 3 hours | 5 hours |
| | Cacao butter | 92.9% | | | | |
| | [Asu$^{1.7}$]eel calcitonin | 0.7 u/sup | 31.0 | 27.6 | 15.1 | 2.3 |
| | Pyroglutamic acid | 7.0% | | | | |
| | Cacao butter | 93.0% | | | | |
| | [Asu$^{1.7}$]eel calcitonin | 0.7 u/sup | 24.3 | 17.6 | 11.3 | 1.4 |
| | Aspartic acid | 7.5% | | | | |
| | Cacao butter | 92.5% | | | | |
| | [Asu$^{1.7}$]eel calcitonin | 0.7 u/sup | 26.2 | 23.1 | 14.3 | 1.8 |
| | Potassium aspartate | 7.5% | | | | |
| | Cacao butter | 92.5% | | | | |
| Control | Ascorbic acid | 7.0% | 0.2 | 0.2 | 0.0 | 0.8 |
| | Cacao butter | 93% | | | | |
| | [Asu$^{1.7}$]eel calcitonin | 0.7 u/sup | 3.2 | 1.2 | 0.6 | 0.8 |
| | Cacao butter | 100% | | | | |
| | [Asu$^{1.7}$]eel calcitonin | 0.7 u/sup | 24.5 | 20.2 | 16.6 | 0 |
| | Phenylglycine ethyl acetoacetate | 7.8% | | | | |
| | Cacao butter | 92.2% | | | | |
| | [Asu$^{1.7}$]eel calcitonin | 0.80 u/sup | 8.5 | 2.6 | 0.3 | 1.2 |
| | Polyoxyethylene sorbitan monosterate | 7.0% | | | | |
| | Cacao butter | 93.0% | | | | |
| | [Asu$^{1.7}$]eel calcitonin (intramuscularly administered) | 0.7 u/kg | 26.0 | 30.5 | 17.5 | 2.1 |

(b) Suppositories containing 0.7 MRC unit of [Aus$^{1.7}$]-eel calcitonin per 80 mg were prepared in the same way as in (a) above by including each of the absorption aids shown in Table 2 in the amounts indicated. Each of the suppositories was intrarectally administered to SD male rats in the same way as in (a) above, and the decrease (%) of the serum calcium level was measured one hour after the administration. The results are shown in Table 2.

TABLE 2

Decrease in serum calcium level

| Absorption aid | Amount of the absorption aid based on the total weight of the suppository (%) | Decrease of the serum calcium level (%) |
|---|---|---|
| Ascorbic acid | 0.8 | 16.0 |
| | 2.4 | 22.3 |
| | 7.0 | 33.1 |
| | 15.0 | 35.1 |
| Glutamic acid | 0.8 | 11.5 |
| | 2.4 | 17.2 |
| | 7.0 | 30.1 |
| | 15.0 | 28.1 |
| Pyroglutamic acid | 0.8 | 15.2 |
| | 2.4 | 20.1 |
| | 7.0 | 31.0 |
| Sodium salicylate | 0.8 | 11.4 |
| | 2.4 | 20.3 |
| | 7.0 | 29.6 |

(c) 0.05 ml of a 0.8% or 2.4% aqueous solution of each of the absorption aids of this invention shown in Table 3 was applied dropwise to one eye of white native male rabbits(body weight 2.0 to 3.0 kg; 3 per group) which, it had been ascertained, were free from any trouble at the cornea, iris and conjunctiva. Nothing was applied to the other eye. Thus, irritation of the absorption aid to the mucous membrane of the eyes were examined, and scores were calculated in accordance with the Draize's eye irritation evaluating method [Association of Foods, Drugs and Cosmetics" (1957)]. The results are shown in Table 3.

As a control, sodium laurylsulfate, a kind of surface-active agent, was evaluated in the same way, and the results are also shown in Table 3.

The results demonstrate that ascorbic acid, glutamic acid, pyroglutamic acid and acetylsalicyclic acid, the absorption aids used in this invention, show almost no irritation, but sodium layrylsulfate used as a control exhibit fairly strong irritation. It is known that the absorption sids used in this invention are either food additives, pharmaceuticals or components of living organisms, and their high level of safety was confirmed also by the above test. On the other hand, the safety of enamine derivatives and surface-active agents has not yet been fully ascertained, and their safety, especially during long-term use, is doubted. The results of the above test strongly suggest the unsatisfactory safety of sodium laurylsulfate.

TABLE 3

Primary irritation scores on the eyes

| (w/v % soln) | Site | \multicolumn{8}{c}{hours after application} |
|---|---|---|---|---|---|---|---|---|---|
| | | 1 | 3 | 6 | 24 | 48 | 72 | 96 | 168 |
| Ascorbic | Cornea | 0 | 0 | 0 | 0 | 0 | 0 | 0 | 0 |
| acid | Iris | 0 | 0 | 0 | 0 | 0 | 0 | 0 | 0 |
| 2.4% | Conjunctiva | 3.3 | 1.3 | 1.3 | 0 | 0 | 0 | 0 | 0 |
| | Total | 3.3 | 1.3 | 1.3 | 0 | 0 | 0 | 0 | 0 |
| L-Glutamic | Cornea | 0 | 0 | 0 | 0 | 0 | 0 | 0 | 0 |
| acid | Iris | 0 | 0 | 0 | 0 | 0 | 0 | 0 | 0 |
| 2.4% | Conjunctiva | 3.3 | 2.0 | 2.0 | 0 | 0 | 0 | 0 | 0 |
| | Total | 3.3 | 2.0 | 2.0 | 0 | 0 | 0 | 0 | 0 |
| DL-Pyroglutamic | Cornea | 0 | 0 | 0 | 0 | 0 | 0 | 0 | 0 |
| acid | Iris | 0 | 0 | 0 | 0 | 0 | 0 | 0 | 0 |

TABLE 3-continued

| (w/v % soln) | Site | Primary irritation scores on the eyes hours after application |  |  |  |  |  |  |  |
|---|---|---|---|---|---|---|---|---|---|
| | | 1 | 3 | 6 | 24 | 48 | 72 | 96 | 168 |
| 2.4% | Conjunctiva | 2.0 | 1.3 | 1.3 | 0 | 0 | 0 | 0 | 0 |
| | Total | 2.0 | 1.3 | 1.3 | 0 | 0 | 0 | 0 | 0 |
| Acetylsalicylic acid | Cornea | 0 | 0 | 0 | 0 | 0 | 0 | 0 | 0 |
| | Iris | 0 | 0 | 0 | 0 | 0 | 0 | 0 | 0 |
| 0.8% | Conjunctiva | 0.7 | 0.7 | 0 | 0 | 0 | 0 | 0 | 0 |
| | Total | 0.7 | 0.7 | 0 | 0 | 0 | 0 | 0 | 0 |
| Sodium Laurylsulfate | Cornea | 0 | 0 | 0 | 0 | 0 | 0 | 0 | 0 |
| | Iris | 0 | 0 | 0 | 0 | 0 | 0 | 0 | 0 |
| 0.1% | Conjunctiva | 4.0 | 4.0 | 0 | 0 | 0 | 0 | 0 | 0 |
| | Total | 4.0 | 4.0 | 0 | 0 | 0 | 0 | 0 | 0 |
| Sodium Laurylsulfate | Cornea | 0 | 0 | 0 | 0 | 0 | 0 | 0 | 0 |
| | Iris | 5.0 | 0 | 0 | 0 | 0 | 0 | 0 | 0 |
| 2.4% | Conjunctiva | 13.3 | 12.7 | 11.3 | 8.0 | 4.0 | 2.7 | 2.0 | 0.7 |
| | Total | 18.3 | 12.7 | 11.3 | 8.0 | 4.0 | 2.7 | 2.0 | 0.7 |

Note:
The scores are averages for three rabbits.

The results obtained in the tests (a), (b) and (c) show that by using the compositions of this invention, calcitonin, an active ingredient substantially unabsorbable in normal intrarectal administration, can be caused to be absorbed very efficiently from the rectum, and that the absorption aids in accordance with the invention for promoting absorption of the active ingredient have very high safety.

EXAMPLE 2

Ascorbic acid (20 g) was added to 180 g of fractionated coconut oil, and the mixture was dispersed using a grinder. Furthermore, 145.5 mg of porcine insulin was added, and the mixture was stirred to form a homogeneous dispersion. 500 mg of the dispersion was filled into a gelatin capsule for suppositories to form a gelatin capsule suppository. One capsule contained 9.6 units of insulin. In the same manner as above, insulin suppositories were prepared using the other absorption aids shown in Table 4 instead of ascorbic acid. The content (units) of insulin and the amounts of the absorption aids and the base (fractionated coconut oil) were as shown in Table 4.

Each of the suppositories was administered intrarectally to white native male rabbits (body weight 3.0 to 3.5 kg; five per group), and the blood glucose level was measured before the administration and 0.5, 1.2, and 3 hours respectively after the administration to examine the absorption of insulin from the rectum. Each time, 0.5 ml of the blood was withdrawn from the ear vein. The glucose level of the blood was measured by the glucose oxidase method.

Table 4 summarizes the decrease (%) of the blood glucose level from that before the administration.

TABLE 4

| | Decrease in blood glucose level | | | | |
|---|---|---|---|---|---|
| | | Decrease (%) in blood glucose level from that before administration | | | |
| Suppository | | 30 minutes | 1 hour | 2 hours | 3 hours |
| Insulin | 9.6 u/sup | 21.2 | 27.8 | 12.2 | 2.3 |
| ascorbic acid | 10% | | | | |
| Fractionated coconut oil | 90% | | | | |
| Insulin | 3.2 u/sup | 31.7 | 39.0 | 14.0 | 2.5 |
| Sodium salicylate | 20% | | | | |
| Fractionated coconut oil | 80% | | | | |
| Insulin | 3.2 u/sup | 9.1 | 22.9 | 35.6 | 8.5 |
| Acetylsalicylic acid | 20% | | | | |
| Fractionated coconut oil | 80% | | | | |
| Insulin | 32 u/sup | 17.3 | 23.5 | 10.0 | 1.7 |
| Sodium glutamate | 13.5% | | | | |
| Fractionated coconut oil | 86.5% | | | | |
| Insulin | 32 u/sup | 16.3 | 21.7 | 8.8 | 2.3 |
| Sodium aspartate | 14.7% | | | | |
| Fractionated coconut oil | 85.3% | | | | |
| Insulin | 9.6 u/sup | 19.3 | 25.7 | 11.5 | 0.7 |
| Sodium ascorbate | 10% | | | | |
| Fractionated coconut oil | 90% | | | | |
| Insulin | 9.6 u/sup | −3.1 | 0.7 | −1.2 | −1.8 |
| Fractionated coconut oil | 100% | | | | |
| Ascorbic acid | 10% | −2.6 | 1.2 | −3.4 | −3.6 |
| Fractionated coconut oil | 90% | | | | |
| Insulin (intramuscularly administered) | 0.32 u/kg | 13.7 | 32.6 | 36.2 | 15.2 |

Note:
The symbol "−" in the above table shows that the blood glucose level increased from that before administration.

EXAMPLE 3

Ascorbic acid (0.65 g) was added to 15.1 g of cacao butter, and they were well mixed in a mortar. Further, 250 mg of heparin sodium was added and mixed well to form a homogeneous composition. The composition was slightly heated to render it flowable, and cast into a container for production of suppositories, followed by solidification at room temperature to form suppositories each having a weight of 1.4 g. One suppository contained about 3700 units of heparin sodium.

The suppositories were intrarectally administered to white native male rabbits having a body weight of 3.0 to 3.5 kg, and variations in the blood coagulation time at 20 minutes, 40 minutes, 1 hour, 2 hours, 3 hours and 4 hours, respectively, after the administration were measured by a partial thromboplastin time. Specifically, the rabbits were used in groups each consisting of five rabbits, and 2.5 ml of the blood was withdrawn each time. 1.8 ml of the blood was immediately placed in a test tube containing 0.2 ml of a 3.8% sodium citrate solution, and centrifuged to obtain plasma for testing.

The results were expressed by the ratio of the blood coagulation time to the blood coagulation time before administration (partial thromboplastin time), and are shown in Table 5.

The above procedure was repeated except that the type and content of the absorption aid were changed. The results are also shown in Table 5.

TABLE 5

| Suppository | | Ratio of the blood coagulating time (partial thromboplastin time) Ratio of the blood coagulating times (determined after the lapse of) | | | | | |
|---|---|---|---|---|---|---|---|
| | | 20 minutes | 40 minutes | 1 hour | 2 hours | 3 hours | 4 hours |
| Sodium heparin | 3700 u/sup | 1.32 | 1.23 | 1.27 | 1.09 | 1.04 | 0.96 |
| Ascorbic acid | 4.1% | | | | | | |
| Cacao butter | 95.9% | | | | | | |
| Sodium heparin | 3900 u/sup | 1.17 | 1.38 | 1.47 | 1.21 | 1.01 | 0.98 |
| Glutamate | 5.9% | | | | | | |
| Cacao butter | 94.1% | | | | | | |
| Sodium heparin | 3300 u/sup | 1.21 | 1.45 | 1.49 | 1.30 | 1.12 | 0.97 |
| Sodium Salicylate | 4.6% | | | | | | |
| Cacao butter | 95.4% | | | | | | |
| Sodium heparin | 3900 u/sup | 1.02 | 0.98 | 0.98 | 1.01 | 1.03 | 0.99 |
| Cacao butter | 100% | | | | | | |
| Ascorbic acid | 4.1% | 1.01 | 1.00 | 0.99 | 1.02 | 0.98 | 1.00 |
| Cacao butter | 95.9% | | | | | | |

EXAMPLE 4

About 10 g of ascorbic acid was added to 190 g of cacao butter, and they were well mixed by a grinder. Then, 28560 MRC units of salmon calcitonin or [Asu$^{1,7}$]-eel calcitonin was gradually added and mixed to form a homogeneous composition. The composition was slightly heated to render it flowable, and poured into a container for production of suppositories, followed by solidification at room temperature to obtain solid suppositories each having a weight of 1.4 g for human application. One suppository contained about 200 MRC units of calcitonin.

EXAMPLE 5

About 20 g of glutamic acid was added to 180 g of a 1:2 mixture of Macrogol (polyoxyethylene glycol) 1000 and Macrogol 4000. Then, 28,560 MRC units of salmon calcitonin or [Asu$^{1,7}$]-eel calcitonin was added gradually and mixed to form a homogeneous composition. The composition was heated to render it flowable, and poured into containers for production of suppositories, followed by solidification at room temperature to obtain solid suppository for humans, each of which had a weight of 1.4 g. One suppository contained about 200 MRC of calcitonin.

EXAMPLE 6

About 20 g of acetylsalicylic acid was dispersed in 1800 g of fractionated coconut oil, and 72,800 MRC units of salmon calcitonin was added, and well stirred in a mixer to obtain a homogeneous dispersion. 500 mg of the dispersion was filled into a gelatin capsule for suppository, to obtain a gelatin capsule suppositories for humans. One capsule contained about 200 MRC units of calcitonin.

What we claim is:

1. A pharmaceutical composition for intrarectal administration comprising a pharmaceutically effective amount of an active ingredient selected from the group consisting of peptide hormones and polysaccharides, which when administered alone to the rectum, is substantially unabsorbable into the living body through the mucous membrane of the rectum, said composition further containing an absorption aid acting within the rectum in such a way as to induce absorption of said active ingredient through the rectal mucous membrane, said absorption aid being characterized by (1) being substantially nontoxic to living organisms, and
(2) having a molecular weight of from about 100 to about 300, and being selected from the group consisting of ascorbic acid or a pharmaceutically acceptable salt thereof, salicylic acid, an ester thereof at its acidic hydroxyl group, or a pharmaceutically acceptable salt thereof at the carboxyl group and pyroglutamic acid, or a pharmaceutically acceptable salt thereof at the carboxyl group.

2. A composition of claim 1 wherein the absorption aid is ascorbic acid or a pharmaceutically acceptable salt thereof.

3. A composition of claim 2 wherein the pharmaceutically acceptable salt of ascorbic acid is sodium or potassium ascorbate.

4. A composition of claim 1 wherein the absorption aid is salicylic acid, an ester thereof at its acidic hydroxyl group, or a pharmaceutically acceptable salt thereof at the carboxyl group.

5. A composition of claim 4 wherein the ester at the acidic hydroxyl group of salicylic acid is acetylsalicylic acid.

6. A composition of claim 4 wherein the pharmaceutically acceptable salt at the carboxyl group is a sodium or potassium salt of salicyclic acid or acetylsalicyclic acid.

7. A composition of claim 1 wherein the absorption aid is pyroglutamic acid.

8. A composition of claim 1 wherein the active ingredient is a peptide hormone.

9. A composition of claim 8 wherein the peptide hormone is calcitonin or insulin.

10. A composition of claim 1 wherein the active ingredient is a polysaccharide.

11. A composition of claim 10 wherein the polysaccharide is heparin.

12. A composition of claim 1 wherein the amount of the absorption aid is about 0.1 to 40% by weight based on the weight of the pharmaceutical composition.

13. A suppository in unit dosage form comprising the pharmaceutical composition of claim 1.

14. A suppository of claim 13 having a solid base capable of becoming flowable in the rectum.

15. A suppository of claim 13 having a substance liquid at room temperature as a main base and being coated with a gelatin film.

* * * * *